US008778911B2

(12) United States Patent
Moulinoux et al.

(10) Patent No.: US 8,778,911 B2
(45) Date of Patent: Jul. 15, 2014

(54) USE OF A POLYAMINE-DEPLETED FOOD COMPOSITION FOR HUMAN OR VETERINARY USE, FOR PREPARING A THERAPEUTIC FOOD PRODUCT

(75) Inventors: Jacques Moulinoux, Rennes (FR); Jean-Pie'rre Estebe, Rennes (FR)

(73) Assignee: Universite De Rennes 1, Rennes Cedex (FR)

( * ) Notice: Subject to any disclaimer, the term of this patent is extended or adjusted under 35 U.S.C. 154(b) by 1300 days.

(21) Appl. No.: 12/161,108

(22) PCT Filed: Jan. 10, 2007

(86) PCT No.: PCT/EP2007/050215
§ 371 (c)(1),
(2), (4) Date: May 5, 2010

(87) PCT Pub. No.: WO2007/082822
PCT Pub. Date: Jul. 26, 2007

(65) Prior Publication Data
US 2010/0286095 A1 Nov. 11, 2010

(30) Foreign Application Priority Data
Jan. 17, 2006 (FR) ...................................... 06 00420

(51) Int. Cl.
*A61K 31/675* (2006.01)
*A61K 31/195* (2006.01)
*A61K 31/132* (2006.01)

(52) U.S. Cl.
USPC .............................. 514/89; 514/564; 514/773

(58) Field of Classification Search
USPC .................... 514/89, 564, 773, 671, 725, 739
See application file for complete search history.

(56) References Cited

U.S. PATENT DOCUMENTS

2007/0184151 A1 * 8/2007 Moulinoux et al. ............ 426/72

FOREIGN PATENT DOCUMENTS

| EP | 0270026 | 6/1988 |
| WO | WO-95/00041 | 1/1995 |
| WO | WO-2005/020974 | 3/2005 |

OTHER PUBLICATIONS

Oram et al. British Medical J. (1961), 1745-1746).*
Thadani (Cardiovascular Drugs and Therapy 18; 339-342 (2004)).*
Proz.com (Jul. 2001) 3 pages.*
Bergeron et al. (Pharmacological Research 38(5) 1998).*
Williams (Biochem J. (1997) 325 :289-297).*
Holliday et al (Publishished in Encyclopedia of Dietary supplements Nov. 2005: Dekker Encyclopedias, Taylor and Francis Publishing).*
Eliassen, Knut A. et al., "Dietary polyamines," *Food Chemistry* 78 2002, 273-280.
Til, H. P. et al., "Acute and Subacute Toxicity of Tyramine, Spermidine, Spermine, Putrescine and Cadaverine in Rats," *Food and Chemical Toxicology* 35 1997, 337-348.
French Search Report with English translation of the International Preliminary Report on Patentability, dated Sep. 9, 2008, (16 pages).
Leung, Jocelyn C. et al., "Expression and developmental regulation of the NMDA receptor subunits in the kidney and cardiovascular system," Am J Physiol Regul Integr Comp Physiol 283: pp. R964-R971, 2002.
Rosenberger, Dorothea et al., "Arrhythmia and neuronal/endothelial myocyte uncoupling in hyperhomocysteinemia," Arch Physiol Biochem, 2006; 112(4-5): pp. 219-227.

* cited by examiner

*Primary Examiner* — Shirley V Gembeh
(74) *Attorney, Agent, or Firm* — Pauly, Devries Smith & Deffner, LLC

(57) ABSTRACT

A polyamine-depleted food compositions is provided for preparing foods, intended for humans or animals, for preventing or treating heart rate anomalies.

25 Claims, 1 Drawing Sheet

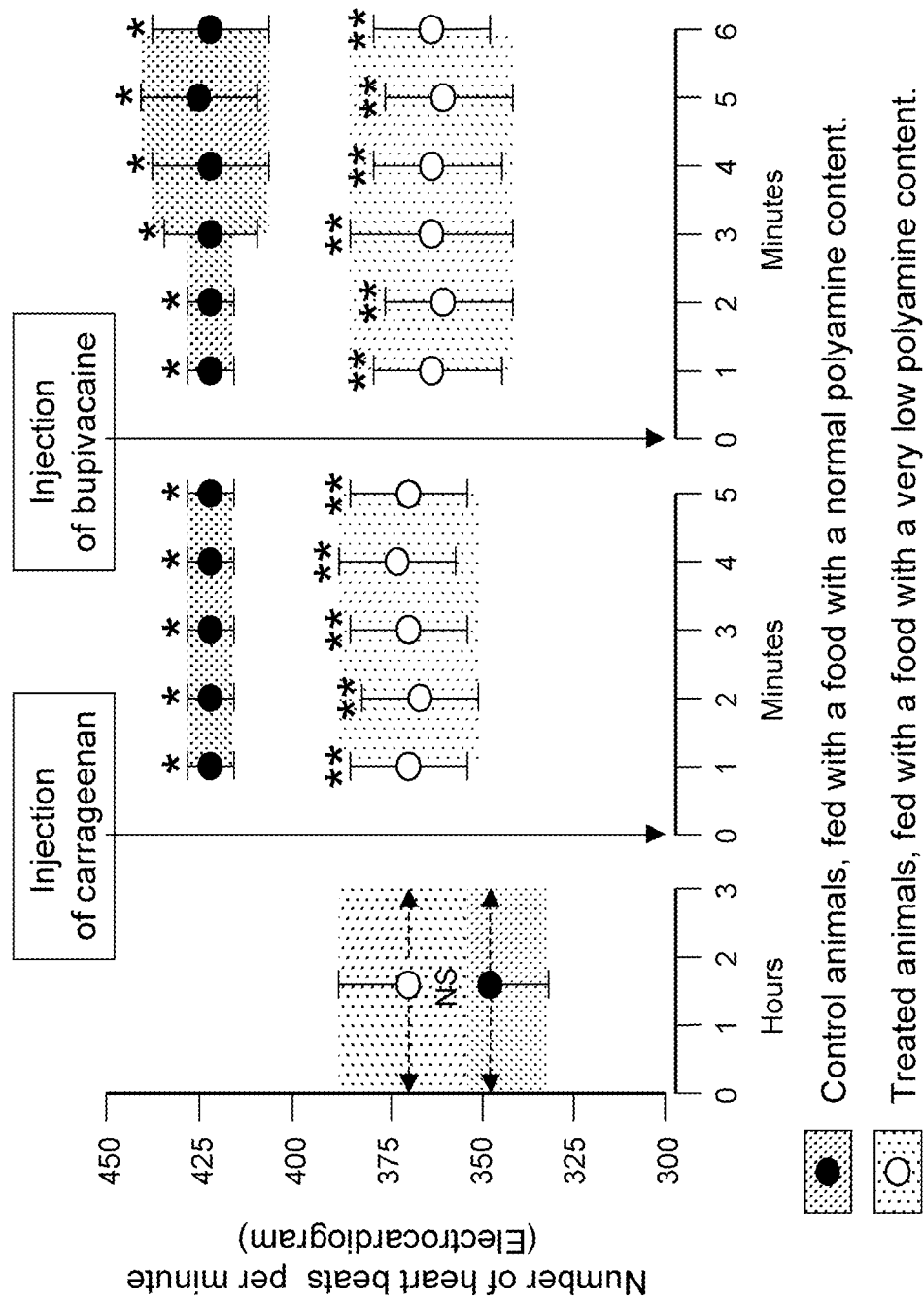

USE OF A POLYAMINE-DEPLETED FOOD COMPOSITION FOR HUMAN OR VETERINARY USE, FOR PREPARING A THERAPEUTIC FOOD PRODUCT

CROSS-REFERENCE TO RELATED APPLICATIONS

This application is a national stage filing of International Patent Application No. PCT/EP2007/050215, filed Jan. 10, 2007, which claims priority to French Patent Application No. 0600420, filed Jan. 17, 2006, both of which applications are hereby incorporated by reference in their entirety.

FIELD OF THE INVENTION

The invention relates to the pharmaceutical and veterinary fields. More specifically, the invention relates to the novel use of polyamine-depleted food compositions for preparing foods, intended for humans or animals, liable to have therapeutic effects.

BACKGROUND OF THE INVENTION

It should be noted that food compositions for human use are known per se and described in WO-9500041 and WO-2005/020974 in the Applicant's name.

Within the scope of WO-9500041, these compositions are used as an anticancer agent (particularly for prostate cancer), to stimulate the immune system, the stimulate NK cell activity, to stimulate endogenous interleukin-2 production, as an analgesic agent and as an agent intended to reduce appetite.

Within the scope of WO-2005/020974, these compositions are used as an agent intended to fight against syndromes or diseases wherein the NR2-B subunit of the N-methyl-D-aspartate receptor is involved.

SUMMARY

The Applicant has now demonstrated that, surprisingly, compositions such as those described in WO-9500041 and WO-2005/020974 could be used to prevent or treat heart rate anomalies.

An aim of the present invention is thus to propose a therapeutic agent liable to prevent or treat heart rate anomalies, irrespective of the aetiology.

Another aim of the present invention is to propose such a therapeutic agent used to fight against anomalies occurring in specific diseases.

An aim of the present invention is also to propose such a therapeutic agent used to control such anomalies occurring after a stress (such as for example an operation) or in cases of addiction.

These aims are achieved by means of the invention which relates to the use of a food composition for human or veterinary use which has less than 1600 picomoles of polyamines, for preparing a therapeutic food product intended to prevent or treat any heart rate anomaly, irrespective of the aetiology.

Such food compositions may be administered by the oral way, but also by the enteral way, for example using a catheter.

BRIEF DESCRIPTION OF THE FIGURES

FIG. 1 is a graph showing the heart rate of Sprague-Dawley rats fed a diet with a normal polyamine content (control animals) or a diet with a very low polyamine content (treated animals) when injected with a 2% carrageenan solution and a 0.25% bupivacaine solution.

DETAILED DESCRIPTION

It is noted that polyamines, particularly putrescine (I), spermidine (II) and spermine (III) are found in all cells.

$^+NH_3—(CH_2)_4—NH_3^+$ (I)
$^+NH_3—(CH_2)_3—NH—(CH_2)_4—NH_3^+$ (II)
$^+NH_3—(CH_2)_3—NH—(CH_2)_4—NH—(CH_2)_3—NH_3^+$ (III)

Although these molecules were considered for a long time to be free from any physiological role and only representing a terminal stage of the tissue catabolism, numerous scientific works have demonstrated that polyamines obtained from orthinine decarboxylation were in fact biological active molecules capable of being involved at various important levels of cell life.

These molecules, which are not only found inside the cells themselves, but also in a circulating state in biological fluids of the body, such as blood, are obtained from three main sources:
 physiological (growth and/or renewal of constituent cells in the body) and tumoral cell proliferation,
 food,
 intestinal bacteria.

Moreover, various works have demonstrated that, in animals, the co-administration of:
 polyamine-free food,
 □-DFMO,
 a polyamine-oxidase (PAO) inhibitor suppressing oxidative back-conversion of spermidine and spermine to putrescine, and
 neomycin and metronidazole.
induces almost-total inhibition of 3LL Lewis lung carcinoma tumoral progression (Seiler N. et al, Cancer Research, 1990, No. 50, pp. 5077-5083), U251 human glioblastoma (Moulinoux J-Ph. et al, Anticancer Research, 1991, No. 11, pp. 175-180), MAT-LyLu Dunning prostate adenocarcinoma (Moulinoux J-Ph. et al, Journal of Urology, 1991, No. 146, pp. 1408, 1412) and neuro 2a human neuroblastoma (Quemener et al, "Polyamines in the gastro-intestinal tract", Dowling R. H., Fölsch I. R. and Löser C Ed., Kluwer Academic Publishers Boston, 1992, pp. 375-385).

Moreover, it has also been demonstrated in animals that polyamine depletion could considerably potentiate the antiproliferative effects of conventional antitumoral drugs (methotrexate, cyclophosphamide, vindesine), while extending the survival time of the animals and could make it possible to reduce the quantities of drugs administered while retaining the same antitumoral effect (Quemener V. et al, "Polyamine deprivation enhances antitumoral efficacy of chemotherapy", Anticancer Research No. 12, 1992, pp. 1447-1454).

Therefore, the present invention aims to cover a novel use of such food compositions, a use which is not evident with respect to the prior art, i.e. the prevention or treatment of heart rate anomalies.

The syndromes and diseases wherein a heart rate anomaly is observed include:
 arrhythmia (tachycardia, bradycardia);
 angina pectoris;
 myocardial infarction;
 trauma;
 operations;
 anxiety;
 stress;

addiction, i.e. dependency on various potentially addictive substances (alcohol, tobacco, drugs, etc.) and compulsive behaviour resulting from this dependency;

excessive physical or mental activity.

Therefore, the present invention is liable to be used to treat or, if need be, to prevent these diseases or syndromes.

In particular, the food compositions in question may be administered to a patient or an animal, prior an operation, in order to prevent any heart rate anomaly during said operation.

Preferentially, the composition used according to the prevent invention contains less than approximately 400 picomoles/g of putrescine, less than 400 picomoles/g of spermidine, less than approximately 400 picomoles/g of spermine and less than approximately 400 picomoles/g of cadaverine.

Preferentially, the composition used according to the present invention contains less than approximately 400, preferentially less than approximately 200, picomoles/g of polyamines.

Advantageously, the composition used according to the present invention contains less than approximately 100, preferentially less than approximately 50, picomoles/g of putrescine, less than approximately 100, preferentially less than approximately 50, picomoles/g of spermidine, less than approximately 100, preferentially less than approximately 50, picomoles/g of spermine and less than approximately 100, preferentially less than approximately 50, picomoles/g of cadaverine. Such a composition provides, daily, at least 17 times less putrescine, 40 times less cadaverine, 70 times less spermidine and 220 times less spermine than the most polyamine-depleted natural human food, but which however meets human nutritional requirements.

According to an alternative embodiment, the composition used according to the present invention also comprises, as a percentage of dry weight with respect to the total dry weight: 10 to 35% fat, 8 to 30% protein, 35 to 80% carbohydrates, up to 10% of a mixture consisting of vitamins, minerals and electrolytes.

Such a composition may be presented in dry form to be dissolved extemporaneously in a neutral vehicle or in ready-to-use liquid form. In any case, the composition is presented in sterile form.

Such a composition is particularly suitable for humans and represents a food substitute which can be used to deplete patients of polyamines effectively. In fact, such a composition makes it possible to feed a patient in a satisfactory manner while inducing a polyamine deficiency, on one hand by inhibiting the synthesis of intracellular polyamines and on the other hand by reducing the exogenous polyamine intake.

Such a composition makes it possible to inhibit endogenous polyamine synthesis and decreases the intake of these compounds very significantly as the various constituent ingredients of said composition are practically free thereof. In order to also decrease polyamine intakes via intestinal bacteria, this composition may be administered concomitantly with a decontamination of the gastrointestinal tract by means of antibiotic(s) and/or antiparasitic(s), such as, for example, neomycin and metronidazole. Moreover, it will be possible to envisage including such antibiotic(s) and/or antiparasitic(s) directly in said composition, without leaving the scope of the invention.

The nutrients used in the food composition according to the invention have a good nutritional value even for ill subjects.

The quantity of water used to prepare the composition used according to the present invention is determined so that the composition is more or less liquid and can be easily ingested by the patient.

The percentage by weight of the mixture consisting of vitamins, minerals and electrolytes is selected so as to comply with the proportions, known to those skilled in the art, required in a balanced diet.

Preferentially, the composition used according to the present invention contains less than 100 picomoles/g of putrescine, less than 100 picomoles/g of spermidine, less than 100 picomoles/g of spermine, less than 100 picomoles/g of cadaverine.

Such a composition may be co-administered with at least one intracellular polyamine synthesis inhibitor.

According to a beneficial alternative embodiment of the invention, the composition used according to the present invention is enriched with at least one intracellular polyamine synthesis inhibitor at a rate of not more than 15% by weight with respect to the total dry weight of the composition and, preferentially, at a rate of a quantity between 0.2% and 7% by weight.

The ODC inhibitors that can be used are particularly chosen from the following compounds:

Pyridoxal phosphate antagonist
L-canaline
N-(5'-phosphopyridoxyl)ornithine
Competitive inhibitors
alpha-hydrazino-ornithine
DK-Alpha-hydrazyno-delta-aminovaleric acid
alpha-methylornithine
trans-3-dehydro-DL-ornithine
1,4-diamino-trans-2-butene
1,4-diaminobutanone
retinol, retinoids, b-carotenes
polyphenols
geraniol
terpenes
flavonoids
procyanidines
resveratrol
Diamine inhibitors
1,3-diaminopropane
1,3-diamino-2-propanol
bis(ethyl)spermine
guanidinobutylamine
Suicide and irreversible inhibitors
2-difluoromethylornithine (DMFO)
monofluoromethylornithine
2-monofluoromethyldehydro-ornithine
2-monofluoromethyldehydro-ornithine methyl ester
5-hexyne-1,4-diamine
trans-hex-2-en-5-yne-1,4-diamine
monofluoromethylputrescine
difluoromethylputrescine
alpha-allenylputrescine
(2R,5R)-6-heptyne-2,5-diamine.

Among these inhibitors, competitive inhibitors are particularly preferred, in particularly alpha-methylornithine (alpha-MO).

Alpha-methylornithine displays numerous advantages within the scope of the use proposed herein. In fact, alpha-MO offers the benefit of being a natural compound which can be easily synthesized and has a high inhibition constant.

Alpha-methylornithine also offers the advantage of inhibiting polyamine synthesis in Escherichia coli, the most common bacterium naturally populating the intestinal tract, which is not the case of DFMO.

In this way, the use of the food composition according to the invention containing alpha-methylornithine as an intracellular polyamine synthesis inhibitor is liable to reduce the exogenous polyamine intake via intestinal bacteria without resorting to the use of antibiotic therapy co-administered with this composition or, at least, by making it possible to reduce the antibiotic dose administered.

Finally, alpha-MO offers the advantage of being a simple competitive ornithine decarboxylase inhibitor and significantly decreases the risks of habituation by the body due to mutation resulting in increased cell resistance.

According to one alternative embodiment, the use of the composition according to the invention is enriched with vitamins, particularly those provided, in healthy humans, by intestinal bacteria. In fact, the antibiotic therapy which may accompany the administration of said composition may also result in a decrease in the intake of certain vitamins. In this case, it may be necessary to enrich the composition used with these vitamins so as not to induce a vitamin deficiency following long-term administration of said composition. In particular, it may be useful to enrich the composition with vitamins or vitamin derivatives. Some vitamin A derivatives (retinoic acid) are in fact ODC activity inhibitors.

Preferentially, the carbohydrates in the composition used belong to the group comprising glucose polymers, maltodextrins, sucrose, modified starches, glucose monohydrate, dehydrated glucose syrup, glycerol monostearate and mixtures thereof. Such carbohydrates are in fact digestible even in cases of digestive disease.

According to an alternative embodiment of the invention, the proteins used belong to the group comprising soluble milk proteins, soya proteins, serum peptides, powdered egg yolk, potassium caseinate, non-phosphorylated peptides, casein peptides, mixed caseinate, soya isolate and mixtures thereof.

Preferentially, the fats belong to the group comprising butter oil, peanut oil, medium-chain triglycerides, grape seed oil, soya oil, oil of evening primrose and mixtures thereof. Advantageously, said fats consist of a mixture of at least one oil of animal origin, at least one oil of vegetable origin and glycerol stearate.

According to an alternative embodiment of the invention, the composition used according to the present invention represents a daily nutritional intake for a human and comprises:
eventually, said intracellular polyamine synthesis inhibitor at a rate of less than 50 g and preferentially at a rate of 1 to 10 g,
between 75 g and 500 g of carbohydrates,
between 20 g and 185 g of fat,
between 20 g and 225 g of protein,
vitamins, minerals and electrolytes in sufficient quantities to meet a human's daily nutritional requirements.

The quantities of vitamins, minerals and electrolytes used are known to those skilled in the art and can be found easily in the literature (see for example, "Apports nutritionnels conseillés", Dupin, Abraham and Giachette, second edition 1992, Ed. TEC et DOC Lavoisier).

Such a composition, used alone, makes it possible to meet a patient's daily nutritional requirements while making it possible to reduce intracellular synthesis and external polyamine intake. Therefore, it represents a food in its own.

Naturally, it may be envisaged to administer such a composition not in a single dose but in several doses spread out during the same day. Each intake will in this case by defined by weight so as to represent a sub-multiple of a human's daily nutritional intake and will comprise:
eventually, said intracellular polyamine synthesis inhibitor at a rate of less than 50/X g and preferentially at a rate of 1/X to 10/X g,
between 75/X g and 500/X g of carbohydrates,
between 20/X g and 185/X g of fat,
between 20/X g and 225/X g of protein,
vitamins, minerals and electrolytes in sufficient quantities to partially meet a human's daily nutritional requirements.

X being an integer between 2 and 8 and corresponding to the number of intakes to be ingested by the patient in order to meet his/her daily nutritional requirements.

The number of such intakes may be chosen so as to completely meet the patient's daily nutritional requirements or be chosen so as to only cover part of its nutritional requirements, the remainder of these requirements being met by natural polyamine-depleted food (ham and pasta or rice, for example).

In this case, the food composition will be used as a food supplement.

The inventors conducted different studies, detailed hereinafter, making it possible to establish in rats that the use of a polyamine-depleted diet made it possible to combat heart rate anomalies.

WORKING EXAMPLE

Twenty male Sprague-Dawley rats with an average weight of 300 g were distributed randomly into two groups of 10 animals. The rats were housed for 2 weeks before testing in an animal store in compliance with European standards.

The studies were conducted within the scope of the Declaration of Helsinki, in accordance with the guidelines issued by the International Association for the Study of Pain.

These two groups of 10 rats (5 per cage) were fed for 4 days (96 hours) before testing:
either with a food with a normal polyamine content, i.e. containing 54 $mg \cdot kg^{-1}$ of putrescine, 27 $mg \cdot kg^{-1}$ of spermidine, 27 $mg \cdot kg^{-1}$ of spermine, 37 $mg \cdot kg^{-1}$ of cadaverine. This group is referred to as the "control group";
or with a food with a very low polyamine content containing less than 10 □g of polyamines per kg of food, synthesised as previously described (Kergozien et al., Life Sci. 1996, 58, 2209-15), in accordance with the recommendations by Cheauveau et al. (Arch. Sci. Physiol., 1951, 5, 305-322), and meeting the daily nutritional requirements of the rodents.

The animals in the control group and the treated group were then subjected to a general anaesthetic by inhalation of 2% halothane (general anaesthetic gas diluted to a rate of 2% with air).

The animals in both groups were then implanted with external electrodes connected to an electrocardiograph.

Electrocardiograms (ECG) were carried out for the first 3 hours after implantation of the electrodes, in order to establish their baseline heart rate.

Three hours after implantation of the heart electrodes, each animal received an injection of 0.2 ml of a 2% carrageenan solution in physiological saline solution in the plantar pad of its rear right paw. Carrageenan is a molecule inducing an inflammatory type pain.

An ECG was performed on each rat every minute, for 5 minutes, immediately after said injection.

The animals then received an injection of 0.5 ml of a 0.25% bupivacaine solution in physiological saline solution on the sciatic nerve path. Bupivacaine is a local anaesthetic. This injection was performed as follows: the right sciatic nerve path was located on each rat via the use of an external nerve stimulator ((HNS 111; Braun Melsungen, Germany). Bupivacaine was then injected on the path of said nerve by means of an insulin needle (Stimuplex A).

Neurological tests were performed to verify the local anaesthesia of the sciatic nerve. Immediately after injection, ECGs were performed on each rat each minute, for 6 minutes.

The main results are recorded in FIG. 1.

During the 3 hours prior to the carrageenan injection, and under general anaesthetic, the baseline heart rate is comparable in the control animals and in the treated animals. No electrocardiographic (ECG) anomalies are detected in either of the animal groups.

Again under general anaesthetic, subsequent to the injection of carrageenan which induces an inflammatory pain in the alert state, the heart rate of the control animals increases very significantly and at an early stage: in the control animals, the heart rate thus changes, less than one minute after the injection of carrageenan, from 350 beats per minute to 425; i.e. a 120% increase of their heart rate (tachycardia).

In the treated animals that received the same injection of carrageenan, also under general anaesthetic, no acceleration of their heart rate is recorded.

Again under general anaesthetic, the local administration of bupivacaine which inhibits the transmission of the nerve influx of the sciatic nerve (motor and sensory nerve) is not accompanied by any significant change in the heart rate, both in the control animals that continue to display tachycardia, and in the treated animals that continue to have a normal heart rate, comparable to that observed prior to the injection of carrageenan.

In the treated animals subject to a reduction in nutritional polyamine intakes for 4 (four) days before the injection of carrageenan, no tachycardia is observed, unlike the control animals fed with a food with a normal polyamine content.

However, these two groups of control and treated animals received an injection of carrageenan under general anaesthetic.

The injection of carrageenan in animals is described extensively in the literature and represents a widely used experimental model.

Similarly, the perception of pain is generally accompanied by an increase in the heart rate. A comparable process occurs in anaesthetised animals: it is known that a painful stimulus may induce tachycardia under general anaesthetic. This is the case following the administration of carrageenan.

In this study, the fact that the control animals under general anaesthetic do not receive a local injection of bupivacaine which inhibits the neuro-transmission of the "pain" information from the periphery (injection of carrageenan) to the central nervous system via the sciatic nerve, which is conveyed by the maintained tachycardia, makes it possible to suggest a central source of the maintenance of said tachycardia.

The invention claimed is:

1. A method for treating a subject suffering from cardiac arrhythmia, comprising:
    administering a food composition which contains less than approximately 400 picomoles/g of putrescine, less than approximately 400 picomoles/g of spermidine, less than approximately 400 picomoles/g of spermine and less than approximately 400 picomoles/g of cadaverine, wherein said composition represents a daily nutritional intake for a human and in that it comprises between 75 g and 500 g of carbohydrates, between 20 g and 185 g of fat, between 20 g and 225 g of protein, and vitamins, minerals and electrolytes in sufficient quantities to meet a human's daily nutritional requirements.

2. The method according to claim 1, wherein said composition further contains less than approximately 400 picomoles/g of polyamines.

3. The method according to claim 1, wherein said composition contains less than approximately 200 picomoles/g of polyamines.

4. The method according to claim 1, wherein said composition contains less than approximately 100 picomoles/g of putrescine, less than approximately 100 picomoles/g of spermidine, less than approximately 100 picomoles/g of spermine and less than approximately 100 picomoles/g of cadaverine.

5. The method according to claim 1, wherein said composition contains less than approximately 50 picomoles/g of putrescine, less than approximately 50 picomoles/g of spermidine, less than approximately 50 picomoles/g of spermine and less than approximately 50 picomoles/g of cadaverine.

6. The method according to claim 1, wherein said composition contains, as a percentage of dry weight with respect to the total dry weight: 10% to 35% fat, 8% to 30% protein, 35% to 80% carbohydrates, up to 10% of a mixture consisting of vitamins, minerals and electrolytes.

7. The method according to claim 6, wherein said composition is enriched with at least one intracellular polyamine synthesis inhibitor at a rate of not more than 15% by weight with respect to the total dry weight of the composition.

8. The method according to claim 7, wherein said composition is enriched with said inhibitor at a rate of between 0.2% and 7% by weight with respect to the total dry weight of the composition.

9. The method according to claim 8, wherein said inhibitor of said composition is a competitive ornithine decarboxylase inhibitor.

10. The method according to claim 9, wherein said competitive inhibitor of said composition is α-methylornithine.

11. The method according to claim 6, wherein said carbohydrates of the composition are selected from the group consisting of glucose polymers, maltodextrins, saccharose, modified starches, glucose monohydrate, dehydrated glucose syrup, glycerol monostearate and mixtures thereof.

12. The method according to claim 6, wherein said proteins of the said composition are selected from the group consisting of soluble milk proteins, soya proteins, serum peptides, powdered egg yolk, potassium caseinate, non-phosphorylated peptides, casein peptides, mixed caseinate, soya isolate and mixtures thereof.

13. The method according to claim 6, wherein said fats of the said composition are selected from the group consisting of butter oil, peanut oil, medium-chain triglycerides, grape seed oil, soya oil, oil of evening primrose and mixtures thereof.

14. The method according to claim 6, wherein said fats of said composition include a mixture of at least one oil of animal origin, at least one oil of vegetable origin and glycerol stearate.

15. The method according to claim 1, wherein said composition contains at least one antibiotic.

16. The method according to claim 1, wherein said composition is enriched with vitamins.

17. The method according to claim 1, wherein said composition represents a daily nutritional intake for a human and in that it comprises:
    less than 50 g and, preferentially, between 1 and 10 g of said intracellular polyamine synthesis inhibitor,
    between 75 g and 500 g of carbohydrates,
    between 20 g and 185 g of fat,
    between 20 g and 225 g of protein, and
    vitamins, minerals and electrolytes in sufficient quantities to meet a human's daily nutritional requirements.

18. The method according to claim 1, wherein said composition is a sub-multiple of a human's daily nutritional intake and in that it comprises:
    between 75/X g and 500/X g of carbohydrates,
    between 20/X g and 185/X g of fat,
    between 20/X g and 225/X g of protein, and vitamins, minerals and electrolytes in sufficient quantities to partially meet a human's daily nutritional requirements, wherein X is an integer between 2 and 8 and corresponding to the number of intakes to be ingested by the patient in order to meet his/her daily nutritional requirements.

19. The method according to claim 1, wherein said composition is a sub-multiple of a human's daily nutritional intake and in that it comprises:

less than 50/X g and, preferentially, between 1/X and 10/X g of said intracellular polyamine synthesis inhibitor, between 75/X g and 500/X g of carbohydrates, between 20/X g and 185/X g of fat, between 20/X g and 225/X g of protein, and vitamins, minerals and electrolytes in sufficient quantities to partially meet a human's daily nutritional requirements, wherein X is an integer between 2 and 8 and corresponding to the number of intakes to be ingested by the patient in order to meet his/her daily nutritional requirements.

20. The method according to claim 1, wherein said composition is presented in a dry form to be dissolved extemporaneously in a neutral vehicle.

21. The method according to claim 1, wherein said composition includes a neutral vehicle rendering it ready for use.

22. The method according to claim 1, wherein said composition is administered as a food substitute.

23. The method according to claim 1, wherein said composition further comprises less than 50 g intracellular polyamine synthesis inhibitor.

24. The method according to claim 1, wherein said composition further comprises between 1 and 10 g of said intracellular polyamine synthesis inhibitor.

25. The method of claim 1, wherein the subject is a human or an animal.

* * * * *